United States Patent
Harrison-Noonan et al.

(10) Patent No.: US 10,206,623 B2
(45) Date of Patent: Feb. 19, 2019

(54) BAND TIGHTNESS SENSOR OF A WEARABLE DEVICE

(71) Applicant: Apple Inc., Cupertino, CA (US)

(72) Inventors: Tobias J. Harrison-Noonan, Cupertino, CA (US); Alex M. Lee, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 600 days.

(21) Appl. No.: 14/867,230

(22) Filed: Sep. 28, 2015

(65) Prior Publication Data

US 2017/0086742 A1    Mar. 30, 2017

(51) Int. Cl.
| | |
|---|---|
| *G01B 21/04* | (2006.01) |
| *A61B 5/00* | (2006.01) |
| *A61B 5/024* | (2006.01) |
| *A61B 5/11* | (2006.01) |

(52) U.S. Cl.
CPC ....... *A61B 5/6843* (2013.01); *A61B 5/02438* (2013.01); *A61B 5/681* (2013.01); *A61B 5/6831* (2013.01); *A61B 5/1118* (2013.01); *A61B 2562/0204* (2013.01); *A61B 2562/0247* (2013.01); *A61B 2562/0261* (2013.01)

(58) Field of Classification Search
CPC ...... B25J 9/1692; G04G 21/02; A61B 5/6843; A61B 5/02438; A61B 5/681; A61B 5/6831; A61B 5/1118; A61B 2562/0204; A61B 2562/0247; A61B 2562/0261; G01L 5/04
See application file for complete search history.

(56) References Cited

U.S. PATENT DOCUMENTS

| | | |
|---|---|---|
| 7,784,366 B2 | 8/2010 | Daverman et al. |
| 8,033,916 B2 * | 10/2011 | Caldwell ............ A63B 69/0002 273/108.2 |
| 8,541,745 B2 * | 9/2013 | Dickinson .............. G04G 21/00 250/340 |
| 8,776,418 B1 | 7/2014 | Martinez et al. |
| (Continued) | | |

FOREIGN PATENT DOCUMENTS

CN       103393411      11/2013

OTHER PUBLICATIONS

Dementyev et al., "WristFlex Low-Power Gesture Input with Wrist-Worn Pressure Sensors," UIST 2014, Oct. 5-8, 2014, Honolulu, Haiwaii, 6 pages.

*Primary Examiner* — Harshad R Patel
*Assistant Examiner* — Nigel H Plumb
(74) *Attorney, Agent, or Firm* — Brownstein Hyatt Farber Schreck, LLP

(57) ABSTRACT

A wearable electronic device has a processing unit and a health sensor included in a housing, a band operable to couple the housing to a body part of a user, and a tightness sensor coupled to the band. The tightness sensor is operable to produce a signal indicative of a tightness of the band on the user's body part. The processing unit determines a tightness of the band based on the signal and perform one or more actions based thereon. Such actions may include evaluating the signal for changes in the tightness of the band according to operational tolerances of the health sensor, providing output directing the user to adjust the band to improve operation of the health sensor, monitoring changes in the tightness of the band and adjusting a measurement obtained by the health sensor, and so on.

20 Claims, 17 Drawing Sheets

(56) References Cited

U.S. PATENT DOCUMENTS

| | | | |
|---|---|---|---|
| 8,781,791 B2* | 7/2014 | Panther | G06F 3/011 |
| | | | 702/160 |
| 8,919,019 B2 | 12/2014 | Martinez et al. | |
| 8,920,332 B2* | 12/2014 | Hong | A61B 5/02427 |
| | | | 600/500 |
| 9,144,273 B2 | 9/2015 | Wu et al. | |
| 9,198,617 B2 | 12/2015 | Kurzweil et al. | |
| 9,274,507 B2* | 3/2016 | Kim | G04G 21/02 |
| 9,282,903 B2 | 3/2016 | Iijima et al. | |
| 9,311,792 B2 | 4/2016 | Kosonen et al. | |
| 9,572,533 B2 | 2/2017 | Venkatraman et al. | |
| 9,781,984 B2* | 10/2017 | Baranski | A44C 5/0069 |
| 9,875,008 B2 | 1/2018 | Cauwels | |
| 9,877,685 B2 | 1/2018 | Kwon et al. | |
| 9,898,120 B2 | 2/2018 | Rhee | |
| 10,061,350 B2 | 8/2018 | Magi | |
| 2005/0075542 A1* | 4/2005 | Goldreich | A61B 5/0205 |
| | | | 600/300 |
| 2006/0100530 A1* | 5/2006 | Kliot | A61B 5/0002 |
| | | | 600/483 |
| 2008/0171915 A1 | 7/2008 | Kawajiri et al. | |
| 2013/0053661 A1* | 2/2013 | Alberth | A61B 5/1455 |
| | | | 600/322 |
| 2013/0172691 A1* | 7/2013 | Tran | A61B 8/488 |
| | | | 600/301 |
| 2013/0231574 A1* | 9/2013 | Tran | A61B 5/0022 |
| | | | 600/479 |
| 2014/0180137 A1* | 6/2014 | Stivoric | A61B 5/0205 |
| | | | 600/484 |
| 2014/0257050 A1 | 9/2014 | Kuroda et al. | |
| 2015/0091711 A1* | 4/2015 | Kosonen | G08B 6/00 |
| | | | 340/407.1 |
| 2015/0173633 A1 | 6/2015 | Shimizu et al. | |
| 2015/0305675 A1* | 10/2015 | Miller | A61B 5/0205 |
| | | | 600/301 |
| 2016/0071408 A1 | 3/2016 | Jiao et al. | |
| 2016/0074649 A1 | 3/2016 | Williams et al. | |
| 2016/0143584 A1 | 5/2016 | Inagaki | |
| 2016/0256116 A1 | 9/2016 | Baik et al. | |
| 2017/0086743 A1* | 3/2017 | Bushnell | A61B 5/6843 |

* cited by examiner

BAND TIGHTNESS SENSOR OF A WEARABLE DEVICE

FIELD

The described embodiments relate generally to wearable electronic devices. More particularly, the present embodiments relate to sensing the tightness of a band attaching a wearable electronic device to a user's body part associated with the operation of a health sensor.

BACKGROUND

Users frequently encounter a variety of different electronic devices in the modern world. Such electronic devices include computers, media players, entertainment systems, displays, communication systems, and so on. Many electronic devices, such as laptop computers, tablet computers, and smart phones, may be portable.

Some electronic devices, referred to as "wearable electronic devices," may be configured to be worn by a user. In some cases, such a wearable electronic device may include one or more bands, straps, or other attachment mechanisms that may be used to attach the wearable electronic device to a user's body part. For example, a wrist worn wearable electronic device may include a band that can be used to secure the wearable electronic device to a user's wrist.

Wearable electronic devices may include a variety of components. For example, such wearable electronic devices may include various sensors, such as sensors that may be used to detect information about the user.

SUMMARY

The present disclosure relates to sensing the tightness of a band attaching a wearable electronic device to a user's body part. A wearable electronic device may have a processing unit and a health sensor included in a housing, a band operable to couple the housing to a body part of a user, and a tightness sensor coupled to the band. The tightness sensor may be operable to produce a signal indicative of a tightness of the band on the user's body part. The processing unit may determine a tightness of the band based on the signal and perform various actions such as evaluating the signal for changes in the tightness of the band according to operational tolerances of the health sensor, providing output directing the user to adjust the band to improve operation of the health sensor, monitoring changes in the tightness of the band and adjusting a measurement obtained by the health sensor, and so on.

In various embodiments, a wearable device may have a housing including a processing unit and a health sensor, a band operable to couple the housing to a body part of a user, and a tightness sensor that is coupled to the band and communicably coupled to the processing unit. The tightness sensor may produce a signal indicating a tightness of the band on the user's body part. The processing unit may be configured to determine the tightness of the band based on the signal and, if the tightness of the band is outside a range of tightness values, provide output directing the user to adjust the band to improve operation of the health sensor.

In some examples, the tightness sensor may include first and second capacitive plates that are operable to change proximity with respect to each other in response to a change in the tightness of the band. In such an example, the signal may indicate a capacitance between the first and second capacitive plates. The first and second capacitive plates may be operable to change proximity with respect to each other in a direction perpendicular to a lengthwise dimension of the band. Alternatively, the first and second capacitive plates may be operable to change proximity with respect to each other to in a direction along a lengthwise dimension of the band.

In various examples, the tightness sensor may include a strain gauge. The strain gauge may be positioned in the band along a lengthwise dimension of the band. The strain gauge may be positioned in a portion of the band where the band attaches to the housing and is disposed perpendicular to a direction of the attachment.

In some embodiments, a wearable device may have a housing including a processing unit and a health sensor, a band operable to couple the housing to a body part of a user, and a tightness sensor that is coupled to the band and is communicably coupled to the processing unit. The tightness sensor may produce a signal indicating a tightness of the band. The processing unit may be configured to monitor changes in the tightness of the band based on the signal and adjust a measurement obtained by the health sensor based on the changes in the tightness of the band to account for movement of the body part.

In various examples, the tightness sensor may include a pressure sensor positioned in an air bladder. The tightness of the band may be related to a pressure in the air bladder.

In some examples, the tightness sensor may include a series of conductors positioned in the band. In such an example, the signal may indicate at least one of a resistance or a capacitance between conductors of the series of conductors. The signal may indicate the resistance between the conductors and the conductors may be positioned along a lengthwise dimension of the band. The signal may indicate the capacitance between conductors and the conductors may be positioned perpendicular to a lengthwise dimension of the band. The signal may indicate both the resistance and the capacitance between the conductors.

In numerous embodiments, a wearable device may have a housing including a processing unit and a health sensor, a band operable to couple the housing to a body part of a user, and a tightness sensor that is coupled to the band and is communicably coupled to the processing unit. The tightness sensor may produce a signal indicating a tightness of the band. The processing unit may evaluate the signal for changes in the tightness of the band according to operational tolerances of the health sensor that relate to the tightness of the band.

In various examples, the tightness sensor may include a capacitive plate disposed in the band that is operable to change proximity with respect to the body part of the user in response to a change in the tightness of the band. The signal may indicate a capacitance between the capacitive plate and the body part of the user.

In some examples, the housing may include an actuator operable to produce a vibration. In such examples, the tightness sensor may detect the vibrations produced by the actuator that travel through at least one of the band or the body part of the user.

In various examples, the housing may include an ultrasonic transmitter operable to produce an ultrasonic signal. In such examples, the tightness sensor may include an ultrasonic receiver that receives the ultrasonic signal through the body part of the user.

In some examples, the tightness sensor may include a microphone. In some cases, the microphone may detect sound waves produced by relative movement of the band and the body part of the user. In various cases, the housing may include a speaker and the microphone may detect sound waves produced by the speaker. In such cases, the signal may indicate a dampening level related to the tightness of the band.

BRIEF DESCRIPTION OF THE DRAWINGS

The disclosure will be readily understood by the following detailed description in conjunction with the accompanying drawings, wherein like reference numerals designate like structural elements.

DETAILED DESCRIPTION

Figure 1A:
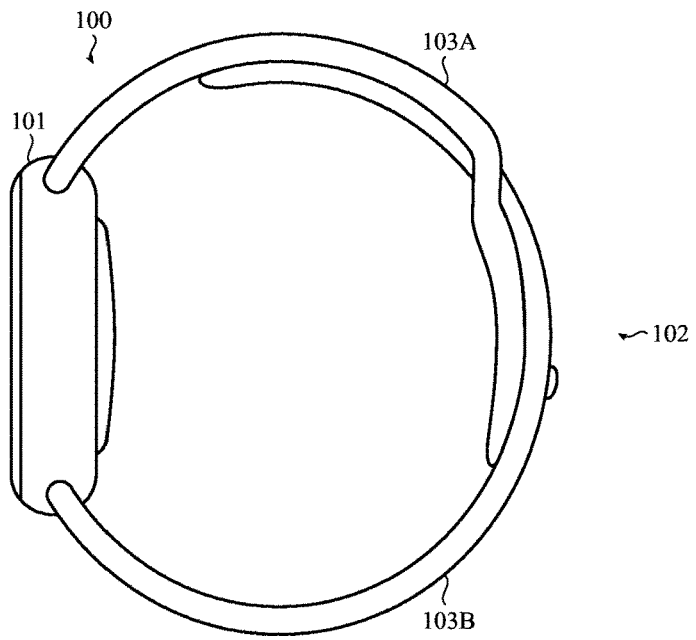
FIG. 1A depicts a wearable electronic device that is operable to determine a tightness of a band.

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The description that follows includes sample systems, methods, and computer program products that embody various elements of the present disclosure. However, it should be understood that the described disclosure may be practiced in a variety of forms in addition to those described herein.

The following disclosure relates to sensing the tightness of a band attaching a wearable electronic device to a user's body part. A wearable electronic device may include a housing having a processing unit and a health sensor, a band operable to couple the housing to a body part of a user, and a tightness sensor coupled to the band that produces a signal indicative of a tightness of the band on the user's body part. The processing unit may determine a tightness of the band based on the signal and perform various operations based thereon.

For example, the processing unit may monitor and/or evaluate the signal for changes in the tightness of the band according to operational tolerances of the health sensor that relate to the tightness of the band. By way of another example, the processing unit may provide output directing the user to adjust the band to improve operation of the health sensor if the tightness of the band is outside a range of tightness values. By way of still another example, the processing unit may monitor changes in tightness of the band and adjust a measurement obtained by the health sensor to account for movement of the body part.

The tightness sensor may be configured in various different implementations. For example, the tightness sensor may include one or more capacitive plates (also encompassing other shaped capacitive elements, flexible sheets, and so on) operable to change proximity with respect to each other in a direction perpendicular to or along a lengthwise dimension of the band. The capacitive plates may form a capacitor whose capacitance changes based on changes in the tightness of the band due to changes in proximity of the capacitive plates resulting from changes in the tightness of the band. By way of another example, the tightness sensor may include a strain gauge positioned in the band along a lengthwise dimension of the band or in a portion of the band where the band attaches to the housing disposed perpendicular to a direction of the attachment. In another example, the tightness sensor may include a pressure sensor positioned in an air bladder whose pressure is related to the tightness of the band. In still another example, the tightness sensor may include a series of conductors positioned in the band whose resistance and/or capacitance changes in response to changes in the tightness of the band. In yet another example, the tightness sensor may detect or receive vibrations or ultrasonic signals transmitted by a component included in the housing through the band and/or the body part of the user. In yet further examples, the tightness sensor may include a microphone that detects sound waves produced by relative movement of the band and the body part of the user and/or produced by a speaker included in the housing that are variously dampened by the tightness of the band.

In some implementations, the tightness sensor may be disposed in other locations rather than coupled to the band. For example, various configurations of tightness sensors may be coupled to the housing and/or included in the housing. In one example, an accelerometer may detect movement related to vibrations produced by an actuator. In another example, one or more force sensors may be positioned on a portion of a housing component coupled to the housing that contacts a user's body part when the wearable electronic device is worn. In still another example, one or more force sensors may couple the housing component to the housing.

These and other embodiments are discussed below with reference to FIGS. 1A-17. However, those skilled in the art will readily appreciate that the detailed description given herein with respect to these Figures is for explanatory purposes only and should not be construed as limiting.

Figure 1B:
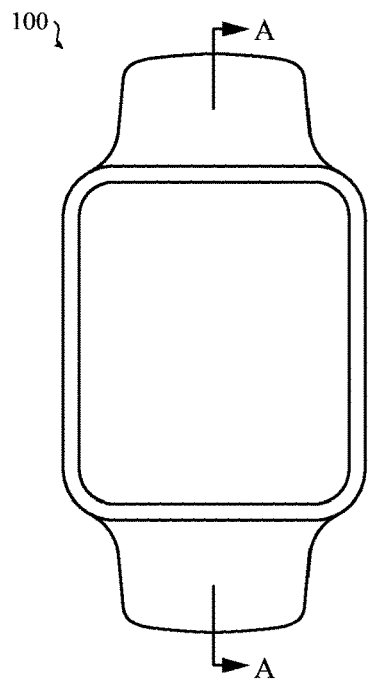
FIG. 1B depicts a front view of the wearable electronic device of FIG. 1A.

FIG. 1A depicts a wearable electronic device 100 that is operable to determine a tightness of a band 102. FIG. 1B depicts a front view of the wearable electronic device 100 of FIG. 1A.

With reference to FIGS. 1A and 1B, the wearable electronic device 100 may include a housing 101 or main body that is operable to be coupled to a body part of a user (such as a wrist) via the band 102 or other attachment mechanism, which may include a first band segment 103A and a second band segment 103B. The wearable electronic device 100 may determine a tightness of the band 102 and perform one or more actions based thereon.

Figure 2:
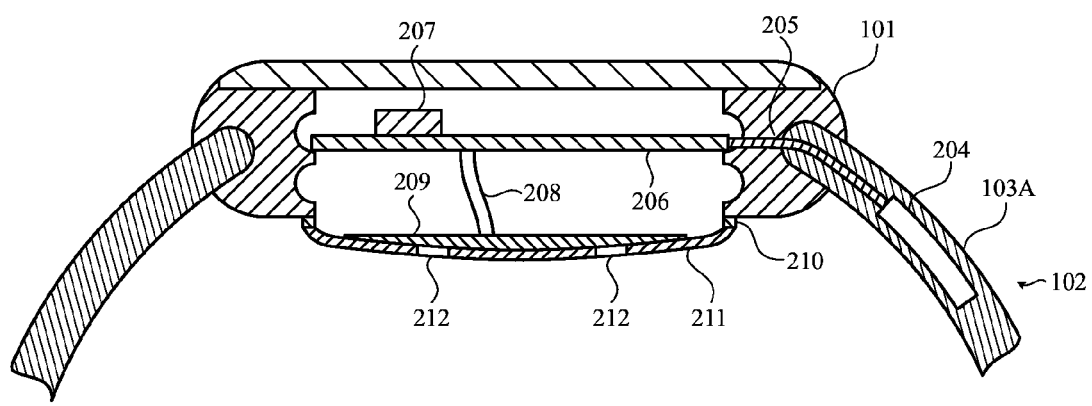
FIG. 2 depicts an example cross-sectional view of the wearable electronic device of FIG. 1B, taken along line A-A of FIG. 1B.

FIG. 2 depicts an example cross-sectional view of the wearable electronic device 100 of FIG. 1B, taken along line A-A of FIG. 1B. The wearable electronic device 100 may include a tightness sensor coupled to the first band segment 103A and communicably connected to a processing unit 207 (such as via a printed circuit board 206 and a flex circuit 205 and/or other electrical connection). In this example, the tightness sensor may include a strain gauge 204.

The strain gauge 204 may be positioned within the band segment 103A along a lengthwise dimension of the first band segment 103A (the dimension running from where the band segment 103A attaches to the housing 101 to where the first band segment 103A is operable to couple to the second band segment 103B). Attaching the housing 101 to a user's body part may exert force on the first band segment 103A related to elongation of the first band segment 103A and/or the entire band 102. This force may strain the strain gauge 204 and the processing unit 207 may receive one or more signals from the strain gauge 204 accordingly. The strain data included in such a signal or signals may be analyzed by the processing unit 207 and correlated to a tightness of the band 102.

The processing unit 207 may use this determined tightness of the band 102 in a variety of ways. The processing unit 207 may use the determined tightness with a health sensor 209 that provides measurements or other data related to the user's body to the processing unit 207 via the printed circuit board 206 and the flex circuit 208 and/or other electrical connection.

By way of example, the health sensor 209 may be a photoplethysmogram (PPG) sensor mounted on a sensor plate 211 or other housing component coupled to the housing 101, such as via adhesive 210. Such a health sensor 209 may emit light through sensor windows 212 in the sensor plate 211 into the user's body part and receive the portion of the transmitted light that is reflected back. The health sensor 209 may transmit measurements regarding the received light to the processing unit 207.

The health sensor's 209 operation may be related to the tightness of the band 102. For example, the health sensor 209 may transmit less accurate measurements if the band 102 is too loose (and/or too tight). Operational tolerances of the health sensor 209 may make the health sensor accurate if the tightness of the band 102 is within a range of tightness values, such as not too loose and/or not too tight. Further, flexing and/or other movement of the user's body part that may change tightness of the band 102 may be incorrectly measured by the health sensor 209 as data relating to other phenomenon, such as blood flow.

In various implementations, the processing unit 207 may evaluate the determined tightness for changes according to operational tolerances of the health sensor 209. The operational tolerances may be operational tolerances of the health sensor 209 that relate to tightness of the band 102, such as whether or not the band 102 is too loose or too tight for the health sensor 209 to operate accurately or whether the user's body part is moving too much for the health sensor 209 to measure accurately.

In some implementations, the processing unit 207 may determine the tightness of the band 102 and provide output directing the user to adjust the first band segment 103A to improve operation of the health sensor 209 if the tightness is outside a range of tightness values. The range of tightness values may represent tightnesses in which the health sensor 209 accurately, or more accurately, operates. Such output may be a visual output via a display component included in the housing 101, an audio output via a speaker or other acoustic component included in the housing 101, a haptic output via a vibration device or other actuator included in the housing 101, a combination of various outputs, and so on.

In various implementations, the processing unit 207 may monitor changes in the tightness of the band 102 and adjust measurements obtained by the health sensor 209. The processing unit 207 may adjust the measurements based on the changes in tightness of the band, such as to account for movement of the user's body part.

For example, the health sensor 209 may provide measurements to the processing unit 207 that the processing unit 207 may analyze to determine blood flow in the user's body part. However, movement of the user's body part (such as movement of a wrist related to a user repeatedly clenching his first) may be measured by the health sensor 209 such that the processing unit 207 misinterprets such measurements as related to blood flow. In such a case, flexing of the user's wrist may be interpreted by the processing unit 207 as the user's pulse rate. Such movement may not be detectable by other movement sensors such as accelerometers, as flexing movements may not change the actual position of the housing 101 and/or other components despite the fact that movement is occurring.

To correct for such movement, the processing unit 207 may screen out measurements corresponding to changes in the tightness of the band 102. In this way, measurements related to actual blood flow may be analyzed in determining blood flow while measurements related to flexing or other similar movement may not be analyzed, resulting in a more accurate determination of information using the health sensor 209.

The strain gauge 204 may be configured to measure strain experienced in multiple directions. For example, the strain gauge 204 may measure strain experienced in the lengthwise direction of the band 102 and strain experienced in the widthwise direction of the band 102 (perpendicular to the lengthwise direction). Measuring strain in multiple directions may allow for screening out of erroneous strain data that relates to temperature variations in the band 102 as opposed to strain data relating to elongation of the band 102 due to tightness.

In some cases, the strain gauge 204 may experience strain due to bending of the band 102 unrelated to the tightness of the band 102. The processing unit 207 may analyze the strain data included in the signal received from the strain gauge 204 to determine strain data indicating of bending as opposed to tightness. In implementations where the processing unit 207 so analyzes the strain data, the processing unit 207 may disregard strain data related to bending as opposed to tightness in determining the tightness of the band 102.

Although the strain gauge 204 is illustrated as embedded in the middle of the first band segment 103A, it is understood that this is an example. In various implementations, the strain gauge 204 may be disposed on a top surface of the first band segment 103A, a bottom surface of the first band segment 103A, and/or otherwise positioned. For example, in various implementations, the strain gauge 204 may include both a strain gauge positioned on a top surface of the first band segment 103A and a strain gauge positioned in a bottom surface of the first band segment 103A in order to more granularly determine the strain experienced at various portions of the band 102 that may relate to the tightness of the band 102.

FIGS. 3-13 depict additional examples in accordance with further embodiments. These additional examples are elaborated in detail below.

Figure 3:
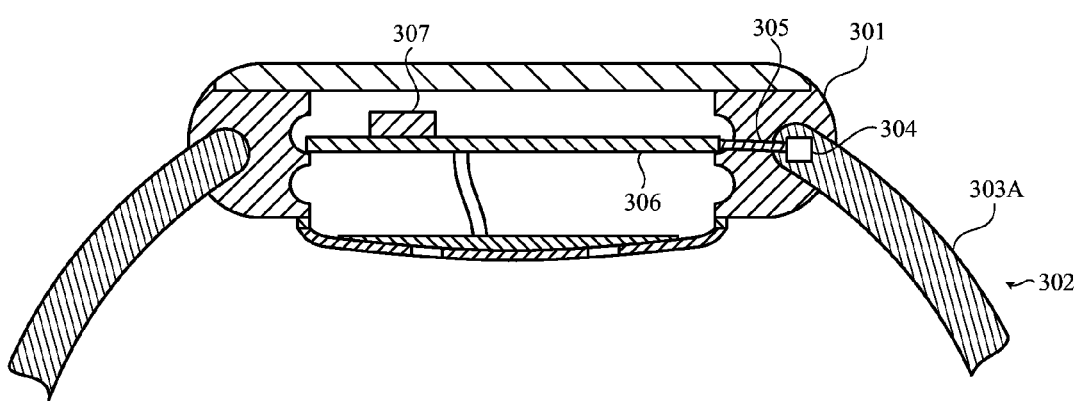
FIGS. 3-13 depict additional examples of the wearable electronic device of FIG. 2 in accordance with further embodiments.

As contrasted with FIG. 2, the example depicted in FIG. 3 positions a strain gauge 304 in a portion of the first band segment 303A where the first band segment 303A attaches to the housing 301. In this example, the attachment is in a direction perpendicular to the lengthwise dimension of the band.

As illustrated, a portion of the housing 301 (and/or associated components) partially surrounds the portion of the first band segment 303A to keep the first band segment 303A coupled to the housing 301 unless the first band segment 303A is moved in a direction perpendicular to the direction of the attachment. As such, tightness of the band 302 may strain the portion of the first band segment 303A (due to how the housing 301 resists decoupling of the first band segment 303A in that direction). This strain may be experienced by the strain gauge 304 and the strain gauge 304 may transmit signals including strain data to the processing unit 307 accordingly via the flex circuit 305 and/or other electrical connection and the printed circuit board 306.

Although this example illustrates and describes the strain gauge 304 as positioned in the portion of the first band segment 303A, it is understood that this is an example. In various implementations, the strain gauge 304 may be positioned on and/or in a portion of the housing 301 adjacent the portion of the first band segment 303A instead of on and/or in the portion of the first band segment 303A.

By way of another example, in some implementations, the first band segment 303A and/or the housing 301 may include various retaining structures operable to resist decoupling of the housing 301 and the first band segment 303A. For example, the first band segment 303A may include a tab that projects to engage a recess of the housing 301 when the first band segment 303A is coupled to the housing 301. In such an example, the tab may be strained by tightness of the band 302 and the strain gauge 304 may be positioned on and/or within the tab.

Figure 4A:
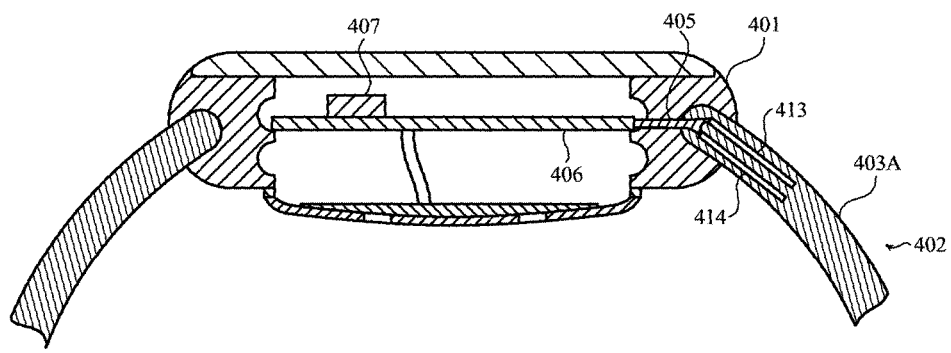
Figure 4B:
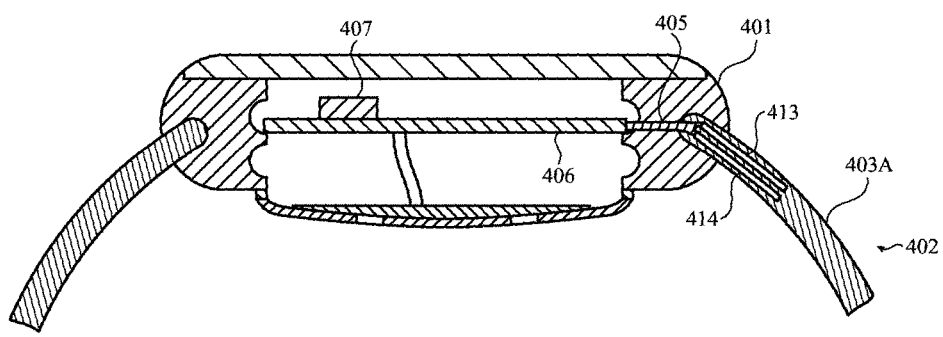

FIG. 4A depicts an example in accordance with further embodiments where the tightness sensor includes first and second capacitive plates 413 and 414 that are operable to change proximity with respect to each other in response to a tightness of the band 402. FIG. 4B depicts tightening of the band 402, resulting in the first and second capacitive plates 413 and 414 moving closer to each other.

With reference to FIGS. 4A and 4B, as the first and second capacitive plates 413 and 414 change proximity with respect to each other, the capacitance between the first and second capacitive plates 413 and 414 may change. In this example, the processing unit 407 positioned within the housing 401 may receive a signal from the first or the second capacitive plate 413 and 414 via the flex circuit 405 and/or other electrical connection and the printed circuit board 406. The signal may include the capacitance, and thus the proximity between the first and second capacitive plates 413 and 414. The processing unit 407 may correlate the capacitance to a tightness of the band 402.

Although this example is illustrated and described as including both the first capacitive plate 413 and the second capacitive plate 414, it is understood that this is an example. In various implementations, the tightness sensor may include a single capacitive plate that changes proximity with respect to the user's body part in response to changes in tightness of the band 402. In such an example, the capacitance may be between the single capacitive plate of the first band segment 403A and the user's body part.

Further, the first and second capacitive plates 413 and 414 are illustrated as oriented such that they are operable to change proximity with respect to each other in a direction perpendicular to the lengthwise dimension of the band 402. However, it is understood that this is an example and that the first and second capacitive plates 413 and 414 may be disposed otherwise in other implementations.

Figure 5:
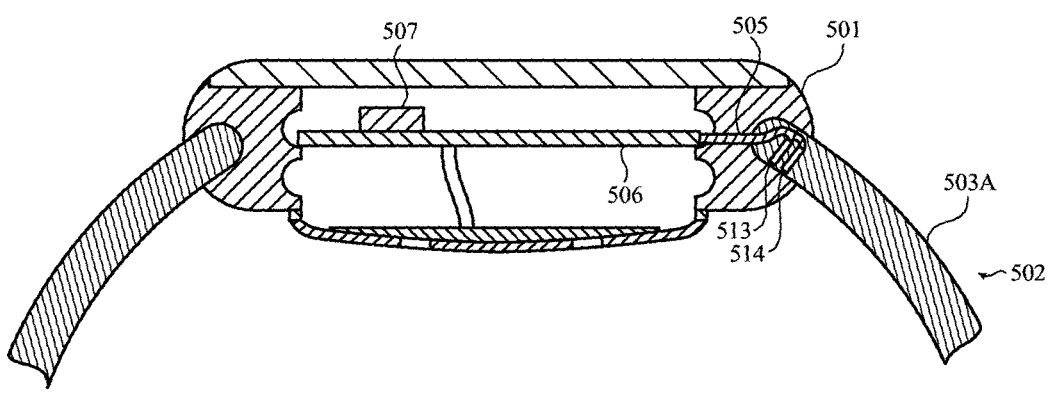

For example, FIG. 5 depicts an example where first and second capacitive plates 513 and 514 are disposed in the first band segment 503A such that they are operable to change proximity with respect to each other in a direction along the lengthwise dimension of the band 502. This change in proximity may be indicated in the signal received by the processing unit 507 via the flex circuit 505 and/or other electrical connection and the printed circuit board 506.

Although this example is illustrated and described as including both the first capacitive plate 513 and the second capacitive plate 514, it is understood that this is an example. In various implementations, the tightness sensor may include a single capacitive plate that changes proximity with respect to the housing 501 in response to changes in tightness of the band 502. In such an example, the capacitance may be between the single capacitive plate of the first band segment 503A and the housing 501.

Figure 6A:
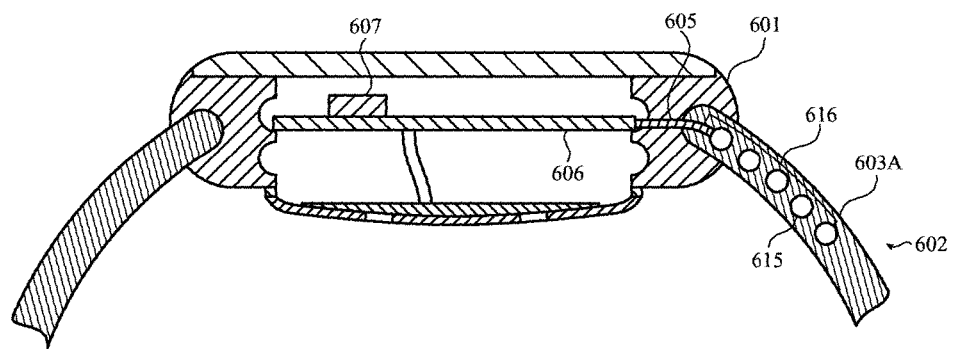
Figure 6B:
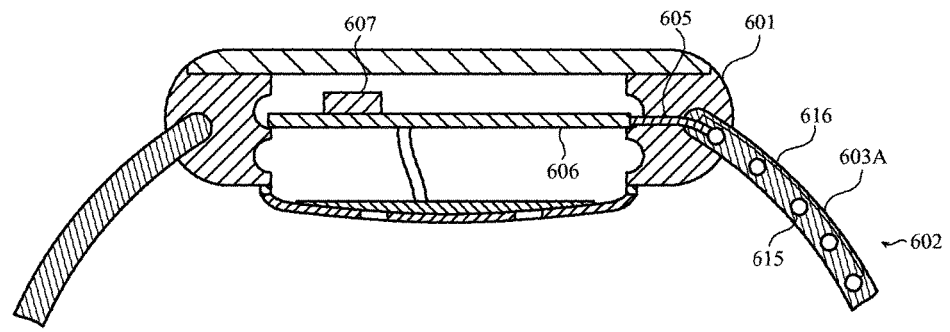

FIG. 6A depicts another example in accordance with further embodiments where the tightness sensor includes a series of conductors 615 (which may be conductive particles) positioned in the first band segment 603A. FIG. 6B depicts tightening of the band 602, resulting in the series of conductors 615 moving further apart from each other (and/or changing dimensions) due to band stretching.

The series of conductors 615 may be connected to the printed circuit board 606 disposed in the housing 601, and thus the processing unit 607, at a first end by the flex circuit 605 and/or other electrical connection and at a second end by a conductor 616 coupled to the flex circuit 605. In this way, the signal may include an indication of a resistance and/or a capacitance across the series of conductors 615. The resistance and/or capacitance across the series of conductors 615 may be dependent on a tightness of the band 602.

For example, with respect to FIGS. 6A-6B, tightening of the band 602 may cause the series of conductors 615 to move further apart. This may cause a resistance across the series of conductors 615 to increase. Conversely, loosening of the band 602 may allow the series of conductors 615 to move closer together. This may cause the resistance to decrease. As such, the processing unit 607 may receive the signal and correlate resistance included in the signal to a tightness of the band 602.

Although a resistance of the series of conductors 615 is described, it is understood that this is an example. In other implementations, one or more other electrical properties of the series of conductors 615 may be used without departing from the scope of the present disclosure, such as capacitance.

As shown, the series of conductors 615 is a single row of conductors 615 positioned along the lengthwise dimension of the band 602. However, it is understood that this is an example. In various implementations, other configurations may be used.

For example, multiple rows of conductors 615 may be positioned above and below each other along the lengthwise dimension of the band 602. As such, tightening of the band 602 may cause conductors 615 adjacent to each other along the lengthwise dimension of the band 602 in one of the rows to move further apart from each other, increasing the resistance between those conductors 615. However, this may cause adjacent rows of conductors 615 above and below each other to at the same time move closer, decreasing the resistance between such adjacent rows of conductors 615. In such an implementation, resistances between conductors 615 in multiple directions may be measured and compared. An increase in resistance in a first direction and a decrease in a second direction may indicate increased tightness whereas a decrease in the first direction and an increase in the second direction indicate decreased tightness. This may allow greater granularity of measurement than in single row implementations, which may allow for greater granularity in determining band 602 tightness.

Alternatively, the series of conductors 615 may be arranged in this way but may be formed of anisotropically conductive particles (such as conductive in the lengthwise direction of the band but not in other directions). In this way, multiple rows may be used without resistance increasing in one direction and decreasing in another.

Further, rather than multiple rows of conductors 615 positioned above and below each other along the lengthwise dimension of the band 602 (and/or in addition to such), one or more rows of conductors 615 may be positioned along the widthwise dimension of the band 602. Resistances, capacitances, and/or other electrical properties across such series of conductors 615 may be monitored as discussed in the other examples above.

For example, rather than a single row of conductors 615 positioned along the lengthwise dimension of the band 602, a single row of conductors 615 may be positioned along the widthwise dimension of the band (perpendicular to the lengthwise dimension of the band 602). The capacitance across the conductors 615 may be measured where an increase indicates tightening of the band 602 and a decrease indicates loosening of the band 602.

Various configurations of conductors 615 are possible and contemplated without departing from the scope of the present disclosure. Further, various electrical properties of the conductors 615 may be monitored and correlated to tightness of the band 602. For example, in some implementations both capacitance and resistance may be measured.

Figure 7:
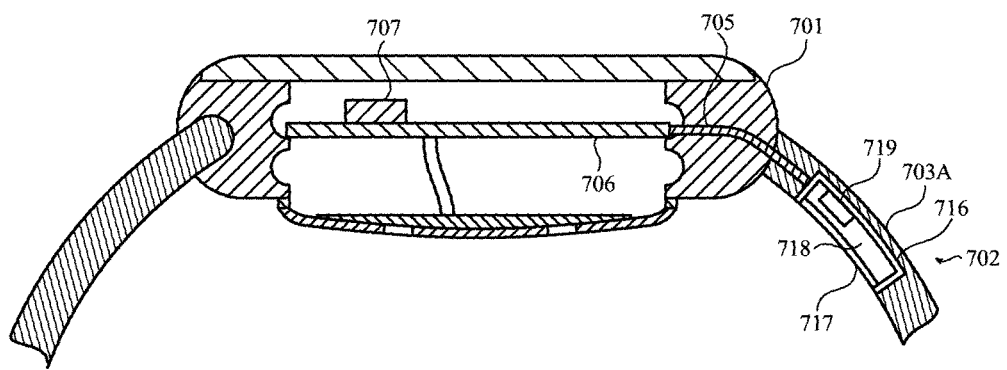

FIG. 7 depicts another example in accordance with further embodiments where the tightness sensor includes a pressure sensor 719 (such as a barometric pressure sensor) positioned in an air bladder 718 (or other cavity) formed by walls 716 and a surface 717. The pressure sensor 719 may transmit signals to the processing unit 707 via the flex circuit 705 and/or other electrical connection and printed circuit board 706 indicating a pressure (such as barometric pressure) in the air bladder 718. The processing unit 707 may correlate the pressure to a tightness of the band 702.

For example, tightening of the band 702 may increase the force exerted between the user's body part and the surface 717. This may increase the pressure in the air bladder 718. Conversely, loosening of the band 702 may decrease the force exerted between the user's body part and the surface 717. This may decrease the pressure in the air bladder 718. Changes in pressure in the air bladder 718 may be indicated in the signals transmitted to the processing unit 707.

In some implementations, one or more components may be coupled to the first band segment 703A and/or the housing 701 that are operable to fill and/or empty the air bladder 718. For example, such a component may include an air compressor, a compressed air cartridge, a valve, and so on.

Figure 8:
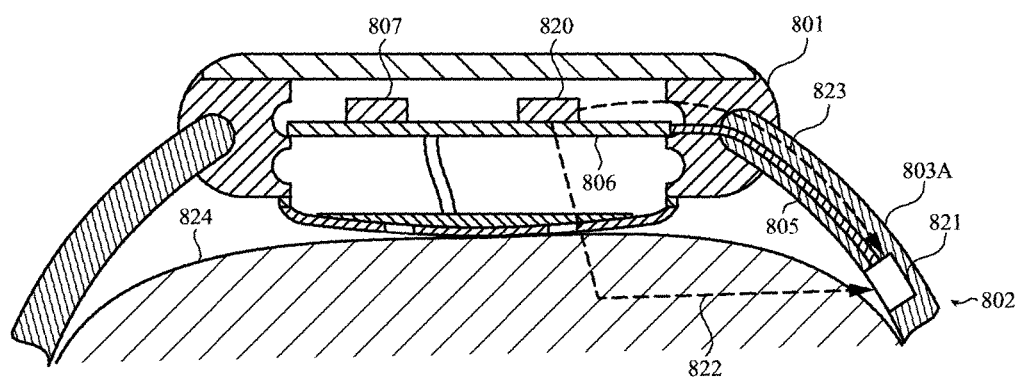

FIG. 8 depicts another example in accordance with further embodiments where the tightness sensor includes a sensor 821 coupled to the first band segment 803A that detects vibrations produced by an actuator 820 disposed on and/or within the housing 801. The signal received by the processing unit 807 via the printed circuit board 806 and the flex circuit 805 and/or other electrical connection may indicate the vibrations received by the sensor 821. The processing unit 807 may correlate the signal to a tightness of the band 802.

The vibrations may travel along and/or through 823 in the first band segment 803A and/or through 822 the body part of the user 824 (such as the user's wrist). Variables involved in the vibrations that are received (such as time, phase shift, dampening, frequency, amplitude, and so on) may be influenced by the tightness of the band 802 and may indicate how tight or loose the band 802 is. As such, the processing unit 807 may analyze the data regarding the received vibrations and correlate the data to a tightness of the band 802.

Figure 9:
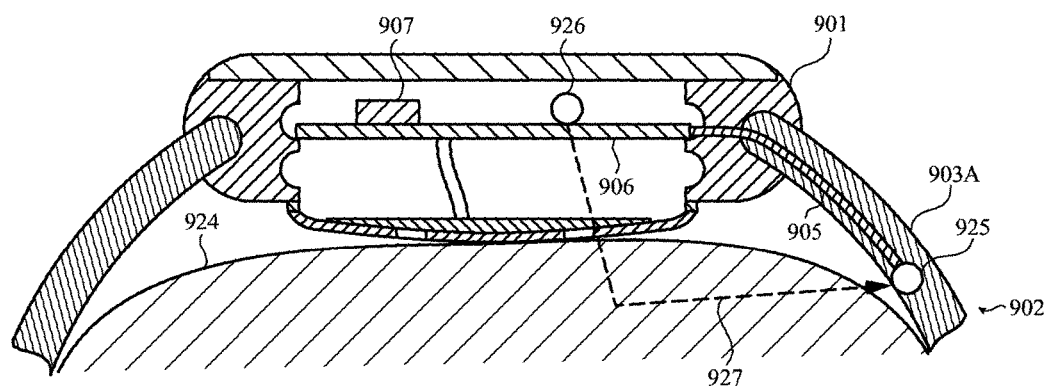

By way of contrast, FIG. 9 depicts an example where the tightness sensor includes an ultrasonic receiver 925 coupled to the first band segment 903A that detects ultrasonic signals produced by an ultrasonic transmitter 926 disposed on and/or within the housing 901. The signal received by the processing unit 907 via the printed circuit board 906 and the flex circuit 905 and/or other electrical connection may indicate the vibrations received by the ultrasonic receiver 925. The processing unit 907 may correlate the signal to the tightness of the band 802.

The ultrasonic signals may travel through 927 the body part of the user 924. Variables involved in the ultrasonic signals that are received (such as time, phase shift, dampening, frequency, amplitude, and so on) may be influenced by the tightness of the band 902 and may indicate how tight or loose the band 902 is. As such, the processing unit 907 may analyze the data regarding the received ultrasonic signals and correlate the data to a tightness of the band 902.

However, it is understood that this is an example. In various implementations, sound waves other than ultrasonic signals may be used without departing from the scope of the present disclosure.

Figure 10:
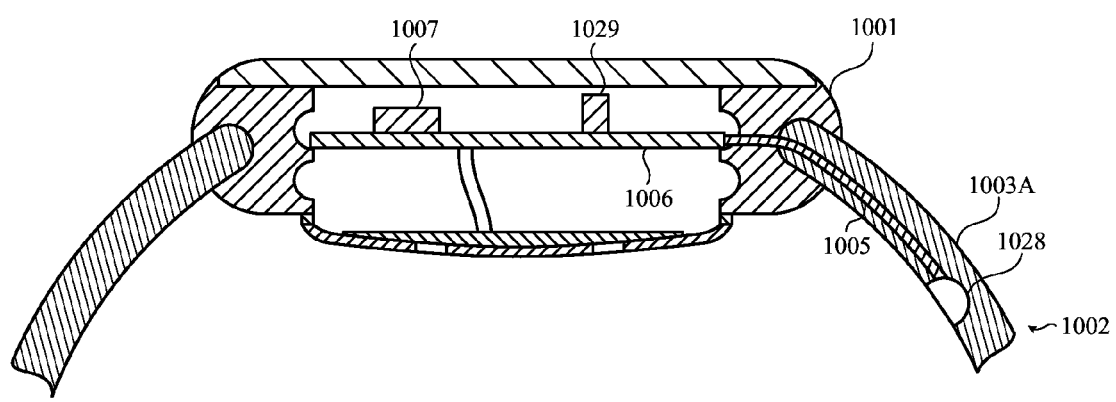

FIG. 10 depicts another example in accordance with further embodiments where the tightness sensor includes a microphone 1028 or other sound wave detector positioned in the first band segment 1003A. The microphone 1028 may receive sound waves produced by relative movement of the band 602 and the body part of the user. The microphone 1028 may transmit signals regarding received sound waves to the processing unit 1007 via the printed circuit board 1006 and the flex circuit 1005 and/or other electrical connection. The processing unit 1007 may analyze the data regarding sound waves in the signal to determine the tightness of the band 1002.

The sound waves may indicate the tightness of the band 1002. For example, the looser the band 1002, the more the band 1002 may be able to move with respect to the user's body part. As such, more sound waves may be produced and detected by the microphone 1028. Conversely, the tighter the band 1002, the less the band 1002 may be able to move with respect to the user's body part. As such, fewer sound waves may be produced and detected by the microphone 1028. The processing unit 1007 may correlate the data regarding sound waves in the signal to a tightness of the band 1002.

Alternatively or additionally, sound waves may produced by a speaker 1029 included in the housing 1001. The microphone 1028 may receive such sound waves and transmit signals regarding such to the processing unit 1007. The microphone's 1028 receipt of the sound waves produced by the speaker 1029 may be variously dampened by the tightness of the band 1002.

For example, the tighter the band 1002, the more dampened the received sound waves may be compared to the sound waves produced. Conversely, the looser the band 1002, the less dampened the received sound waves may be compared to the sound waves produced. The processing unit 1007 may correlate the data in the signal regarding the sound waves received versus the sound waves produced to determine the tightness of the band 1002.

Although FIGS. 1-10 are illustrated and described as including tightness sensors coupled to the first band segments 103A-1003A, it is understood that these are examples. In various implementations, tightness sensors may be otherwise positioned.

Figure 11:
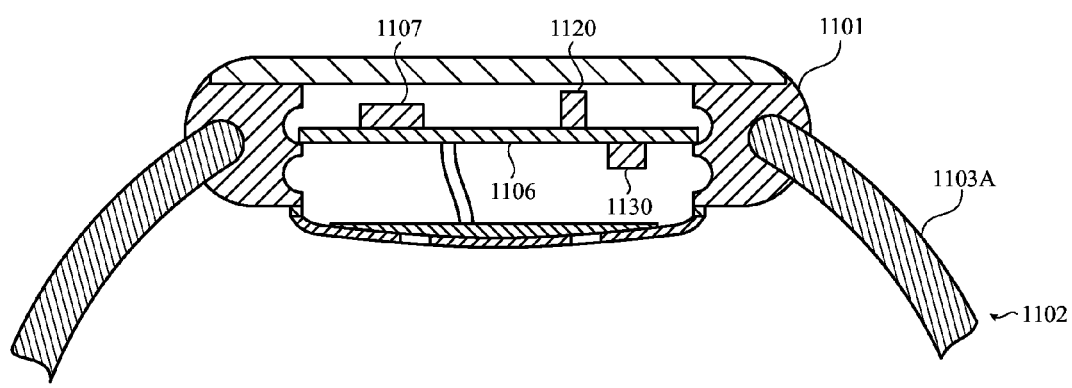

For example, FIG. 11 depicts an example tightness sensor including a sensor 1130 disposed in the housing 1101 instead of coupled to the first band segment 1103A that detects vibrations produced by an actuator 1120. The signal received by the processing unit 1107 via the printed circuit board 1106 may indicate the vibrations received by the sensor 1130. The processing unit 1107 may correlate the signal to the tightness of the band 1102. Variables involved in the vibrations that are received (such as time, phase shift, dampening, frequency, amplitude, and so on) may be influenced by the tightness of the band 1102 based on how much the housing 1101 may move in response to the vibrations and may indicate how tight or loose the band 1102 is. As such, the processing unit 1107 may analyze the data regarding the received vibrations and correlate the data to a tightness of the band 1102.

Figure 12:
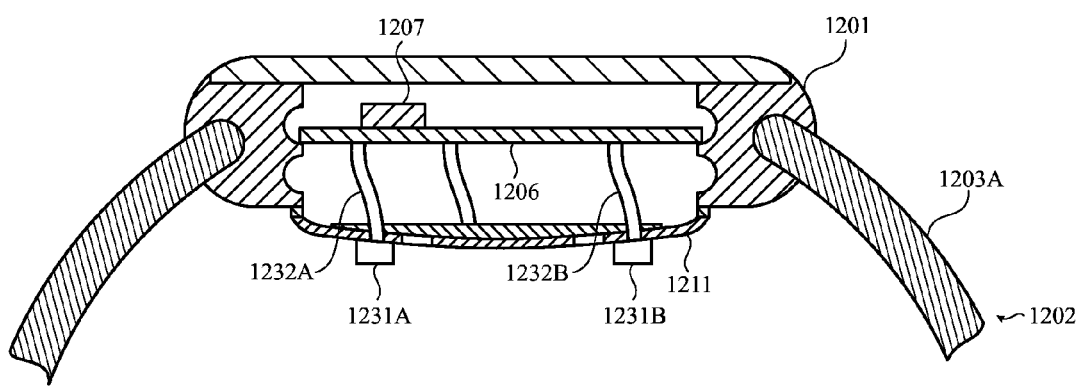

By way of another example, FIG. 12 depicts an example tightness sensor including force or pressure sensors 1231A and 1231B disposed on a surface of the sensor plate 1211 coupled to the housing 1201. The amount of force exerted between a user's body part and the force or pressure sensors 1231A and 1231B may be related to the tightness of the band 1202. As such, the processing unit 1207 may receive signals from the force or pressure sensors 1231A and 1231B related to the exerted force via the printed circuit board 1206 and the flex circuit 1205 and/or other electrical connections. The processing unit 1207 may correlate data in the signals related to the exerted force to determine the tightness of the band 1202.

The force determined by the processing unit 1207 by analyzing signals may be a non-binary value. The processing unit 1207 may analyze the signals to determine forces across a range of force values as opposed to detecting that a threshold amount of force is exerted. The processing unit may analyze force signals to correlate data in the signals to an amount of force applied out of a range of possible forces.

Although FIG. 12 illustrates force or pressure sensors 1231A and 1231B disposed on a surface of the sensor plate 1211, it is understood that this is an example. Various numbers of force or pressure sensors 1231A and 1231B and/or other force or pressure sensors may be variously disposed without departing from the scope of the present disclosure. For example, a set of contact force sensors (which may be any kind of contact force sensors) on an inner surface of the band 1202 that faces the user's body part without departing from the scope of the present disclosure.

Figure 13:
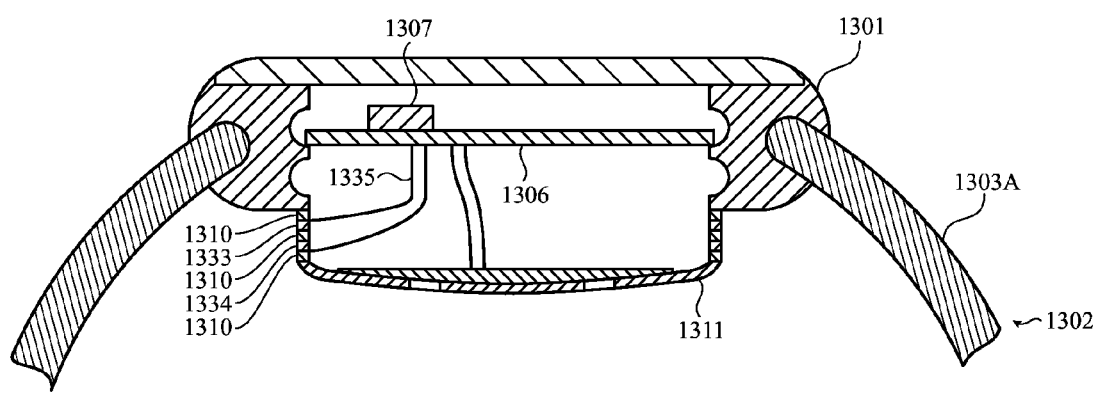

By way of still another example, FIG. 13 depicts an example tightness sensor including a force sensor having first and second capacitive plates 1333 and 1334 disposed between the sensor plate 1311 and the housing 1301. The amount of force exerted between a user's body part and the sensor plate 1311 may be related to the tightness of the band 1302. As such, the processing unit 1307 may receive signals via the printed circuit board 1306 and the flex circuit 1335 and/or other electrical connections related to the exerted force. The processing unit 1307 may correlate data in the signals related to the exerted force to determine the tightness of the band 1302.

The first and second capacitive plates 1333 and 1334 may be operable to change proximity with respect to each other. The first and second capacitive plates 1333 and 1334 may be coupled to each other and to the housing 1301 and the sensor plate 1311, respectively, via adhesive 1310. Tightening of the band 1302 may exert force between the user's body part and the sensor plate 1311, compressing the adhesive 1310 between the first and second capacitive plates 1333 and 1334 and allowing the first and second capacitive plates 1333 and 1334 to become more proximate to each other. Conversely, loosing of the band 1302 may allow the first and second capacitive plates 1333 and 1334 to move further apart. The capacitance between the first and second capacitive plates 1333 and 1334 may change as the proximity of the first and second capacitive plates 1333 and 1334 changes. The processing unit 1307 may correlate the capacitance to a tightness of the band 1302.

Although the above examples are illustrated and described in the context of attachment mechanisms such as bands for attaching wearable electronic devices to body parts of users, it is understood that this is an example. In various implementations, the disclosed techniques may be used to determine tightness of attachment mechanisms that attach electronic devices to other objects, such as a mounting apparatus operable to mount a display device to a car dash board.

Figure 14:
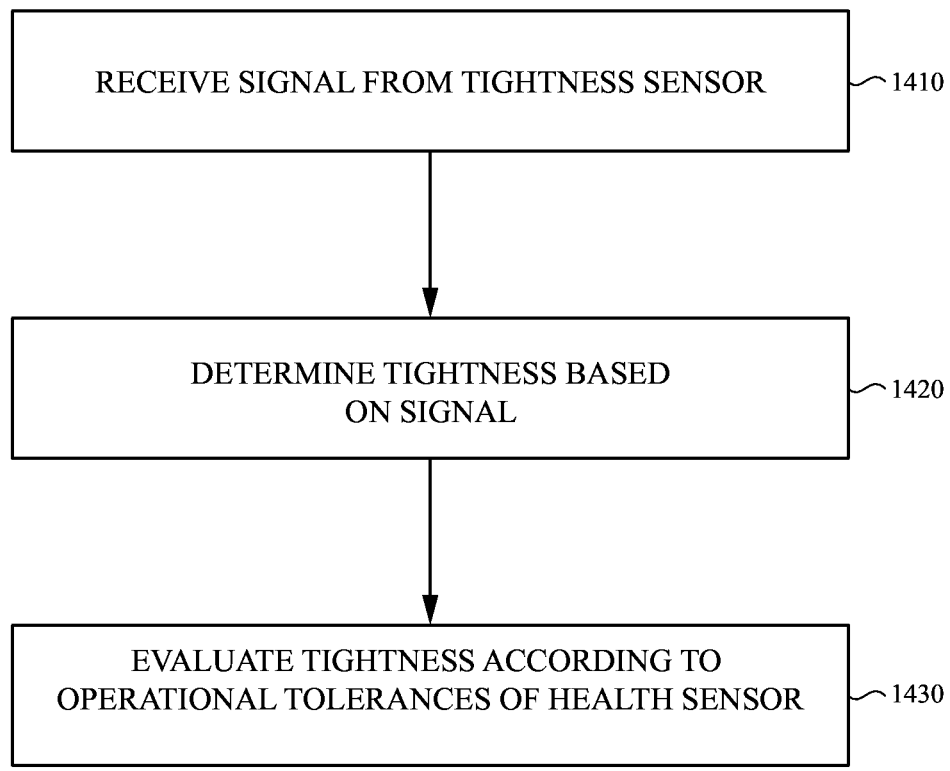
FIG. 14 depicts a flow chart illustrating an example method for using a band tightness sensor with a health sensor. The method may be performed by one or more of the wearable electronic devices of FIGS. 1A-13.

FIG. 14 depicts a flow chart illustrating an example method 1400 for using a band tightness sensor with a health sensor. The method 1400 may be performed by one or more of the wearable electronic devices of FIGS. 1A-13.

At 1410, a signal may be received from a tightness sensor. The tightness sensor may be coupled to the band of a wearable electronic device that is operable to couple the wearable electronic device to the body part of a user. The signal may include data indicative of a tightness of the band.

At 1420, a tightness of the band may be determined based on the signal. A processing unit may correlate data in the signal to band tightness.

At 1430, the determined tightness may be evaluated according to operational tolerances of a health sensor. For example, if the determined tightness is outside an operational range of the health sensor for optimal or accurate health sensor operation, instructions to adjust the band may be output to a user. By way of another example, the determined tightness may indicate changes in tightness caused by user body part movement that may be interpreted by the health sensor as indicative of other health information related to the user's body part. In such an example, the processing unit may use the determined tightness to screen out erroneous data from health information determinations.

Although the example method 1400 is illustrated and described as including particular operations performed in a particular order, it is understood that this is an example. In various implementations, various orders of the same, similar, and/or different operations may be performed without departing from the scope of the present disclosure.

For example, the example method 1400 is described as receiving the signal from a tightness sensor coupled to a band of a wearable electronic device. However, in various implementations, the tightness sensor may be otherwise coupled. For example, the tightness sensor may be coupled to a housing or main body of the wearable electronic device without departing from the scope of the present disclosure.

Figure 15:
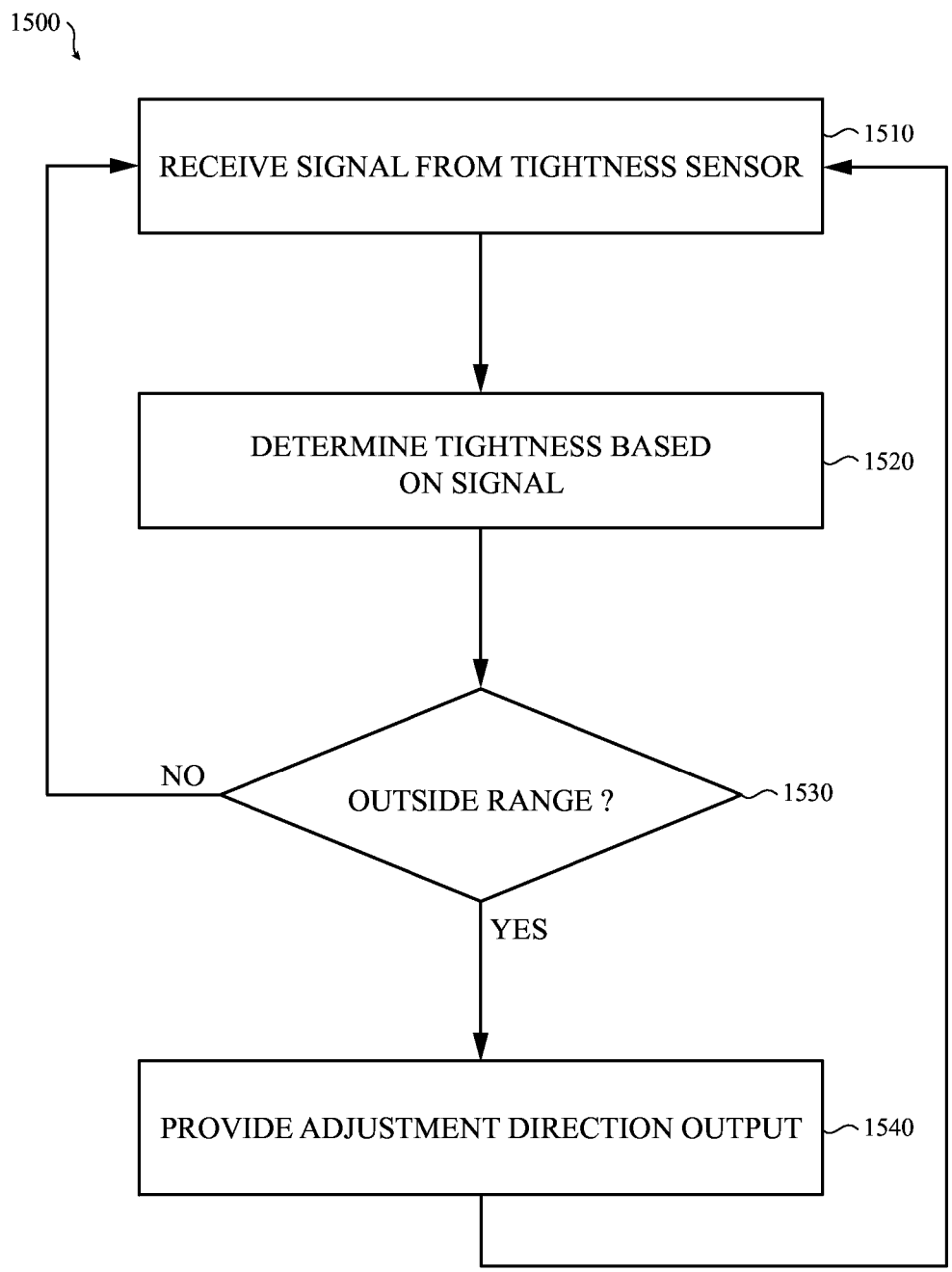
FIG. 15 depicts a flow chart illustrating an example method for directing a user to adjust band tightness. The method may be performed by one or more of the wearable electronic devices of FIGS. 1A-13.

FIG. 15 depicts a flow chart illustrating an example method 1500 for directing a user to adjust band tightness. The method 1500 may be performed by one or more of the wearable electronic devices of FIGS. 1A-13.

At 1510, a signal may be received from a tightness sensor. The tightness sensor may be coupled to the band of a wearable electronic device that is operable to couple the wearable electronic device to the body part of a user. The signal may include data indicative of a tightness of the band. At 1520, a tightness of the band may be determined based on the signal. A processing unit may correlate data in the signal to a band tightness.

At 1530, it may be determined whether or not the determined tightness of the band is within a range of tightness values. The range of tightness values may be a range of band tightnesses within which a health sensor accurately or optimally operates. For example, the range of tightness values may be a range of tightnesses that are defined as not too tight and not too loose. If the tightness is not outside the range of tightness values, the flow may return to 1510 where the signal continues to be received. Otherwise, the flow may proceed to 1540.

At 1540, adjustment direction output may be provided. The adjustment direction output may include a visual output, an audio output, a haptic output such as vibrations, a combination of various outputs, and so on. In some examples, the output may indicate that the band tightness is outside the range of tightness values and should be adjusted to improve health sensor operation. In other examples, the output may specify whether the band should be tightened or loosened. In various examples, the adjustment direction output may be transmitted to one or more other electronic devices.

Although the example method 1500 is illustrated and described as including particular operations performed in a particular order, it is understood that this is an example. In various implementations, various orders of the same, similar, and/or different operations may be performed without departing from the scope of the present disclosure.

For example, the example method 1500 is illustrated and described as providing adjustment direction output. However, in various implementations, the band may include one or more tightness adjustment mechanisms controllable by the processing unit, such as a memory wire that is operable to tighten and/or loosen the band under the application of electrical current. In such an implementation, the processing unit may control the tightness adjustment mechanism to adjust tightness of the band to be within the range of tightness values rather than instructing a user to adjust the band.

Figure 16:
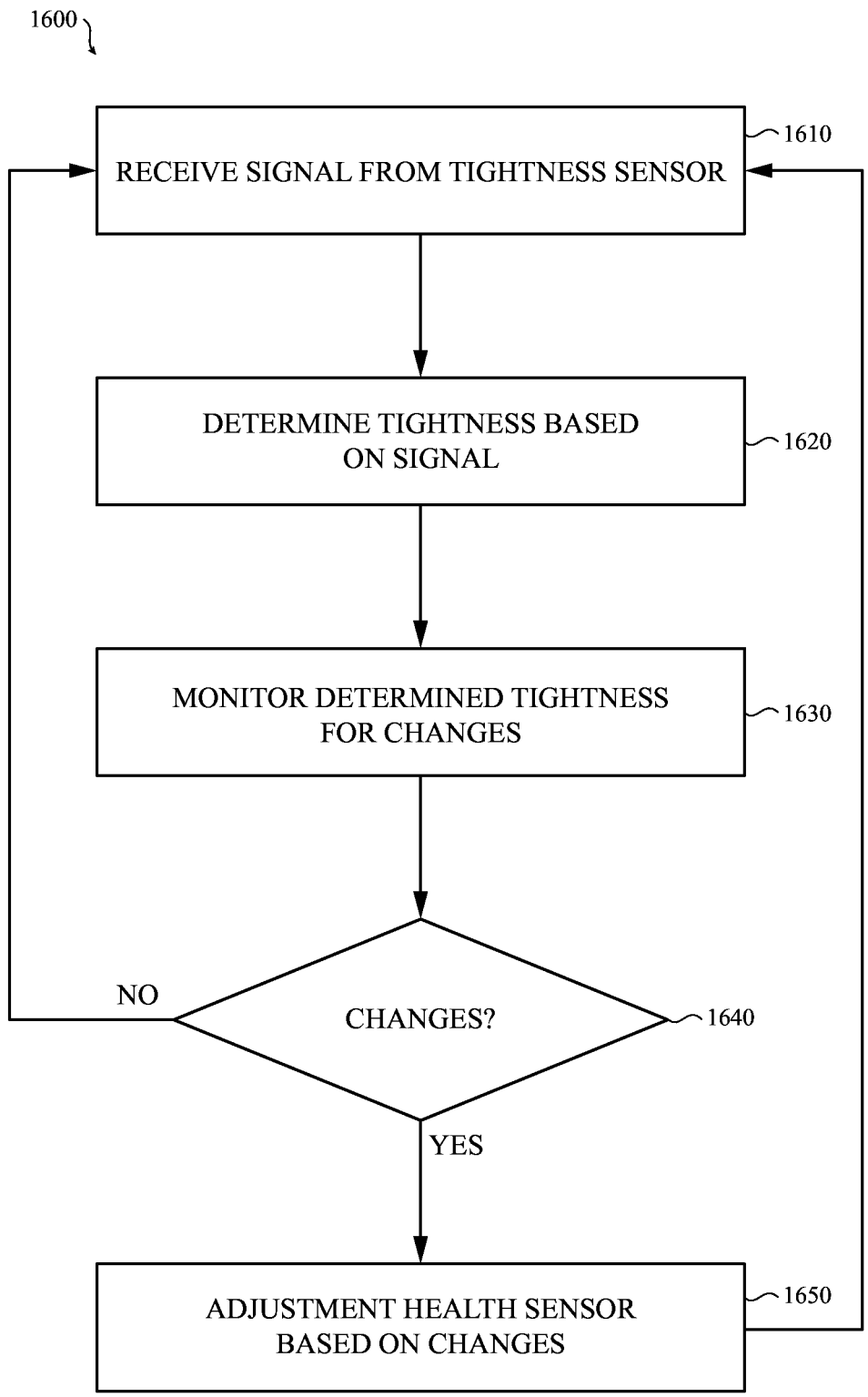
FIG. 16 depicts a flow chart illustrating an example method for adjusting a health sensor measurement based on band tightness. The method may be performed by one or more of the wearable electronic devices of FIGS. 1A-13.

FIG. 16 depicts a flow chart illustrating an example method 1600 for adjusting a health sensor measurement based on band tightness. The method 1600 may be performed by one or more of the wearable electronic devices of FIGS. 1A-13.

At 1610, a signal may be received from a tightness sensor. The tightness sensor may be coupled to the band of a wearable electronic device that is operable to couple the wearable electronic device to the body part of a user. The signal may include data indicative of a tightness of the band. At 1620, a tightness of the band may be determined based on the signal. A processing unit may correlate data in the signal to a tightness of the band.

At 1630, the determined tightness may be monitored for changes. For example, the determined tightness may be compared to the previous determined tightness, or to a sequence of previous determined tightnesses, to determine whether or not the determined tightness has changed. The determined tightness may have changed if the band became tighter or looser since a previous determined tightness.

At 1640, it may be determined whether or not the determined tightness has changed. If not, the flow may return to 1610 where the signal continues to be received. Otherwise, the flow may proceed to 1650.

At 1650, measurements obtained from a health sensor may be adjusted based on the determined changes. For example, changes in tightness may be caused by user body part movement and may be interpreted by the health sensor as indicative of other health information related to the user's body part. In such an example, the determined tightness changes may be used to screen out erroneous data from health information determinations.

By way of another example, a health sensor may not obtain accurate measurement when the user's body part is moving. In such an example, any health sensor measurements obtained when the tightness was determined to have changed may be disregarded in favor of measurements obtained when the tightness was not determined to have changed. This may result in more accurate determinations based measurements from the health sensor.

Although the example method 1600 is illustrated and described as including particular operations performed in a particular order, it is understood that this is an example. In various implementations, various orders of the same, similar, and/or different operations may be performed without departing from the scope of the present disclosure.

For example, the example method 1600 is illustrated and described as adjusting measurements obtained from the health sensor based on changes in band tightness. However, in some implementations, measurements obtained from a health sensor may be scaled and/or otherwise adjusted based on determined band tightness without regard to whether or not the tightness of the band is determined to change over time.

By way of another example, the example method 1600 is illustrated and described as being performed continuously. However, in various implementations, one or more portions of the method may be performed at various times, intervals, and so on. For example, in some implementations, the example method 1600 may be performed when the health sensor is operating. In other implementations, the example method 1600 may be performed at particular specified times or intervals (which may be user specified). In still other implementations, the example method 1600 may be performed in response to user input indicating to perform the example method 1600.

Figure 17:
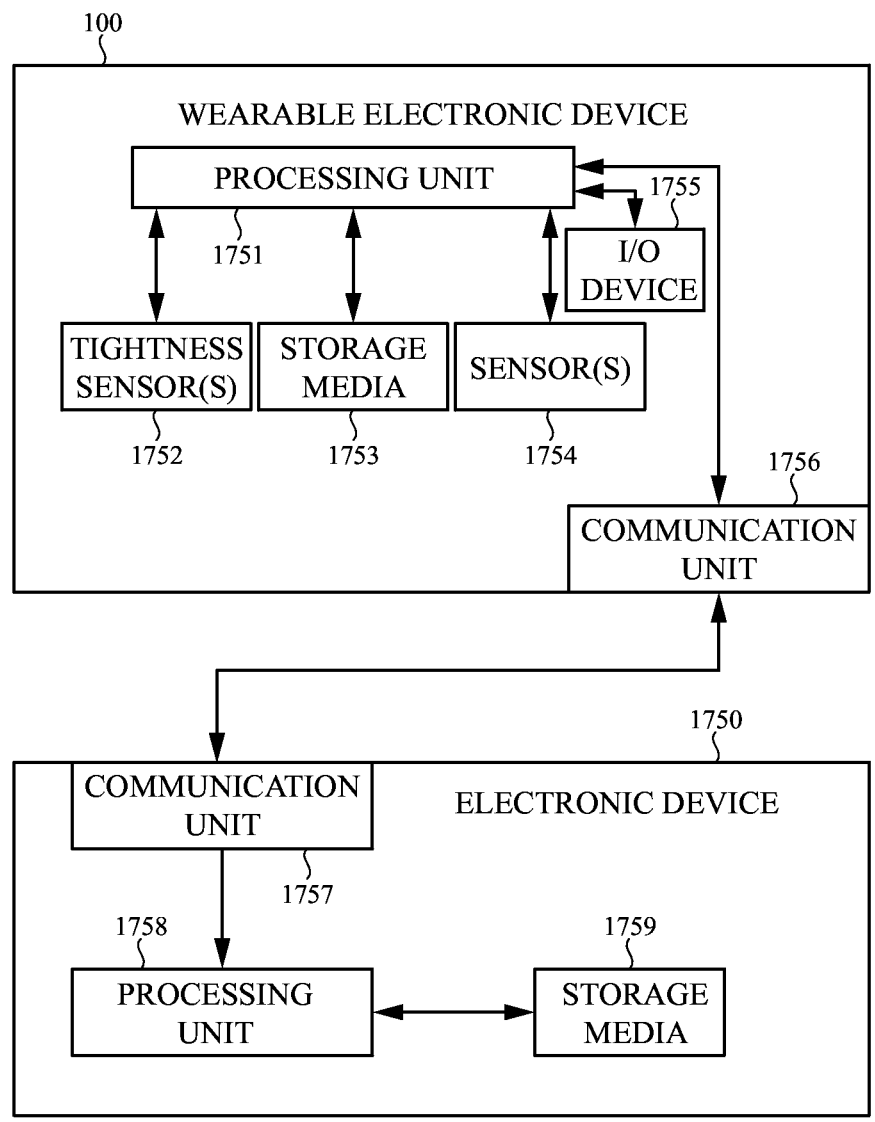
FIG. 17 depicts a block diagram illustrating example components that may be utilized in the wearable electronic device and example functional relationships of those components.

FIG. 17 shows a block diagram illustrating example components that may be utilized in the wearable electronic device 100 of FIGS. 1A-1B and example functional relationships of those components. The wearable electronic device 100 may include one or more processing units 1751, tightness sensors 1752 (such as those discussed above), storage media 1753 (such as a magnetic storage medium, an optical storage medium, a magneto-optical storage medium, a read only memory, a random access memory, an erasable programmable memory, and so on), one or more other sensors 1754 (such as one or more health sensors, accelerometers, gyroscopes, light sensors, cameras, proximity sensors, touch sensors, and so on), one or more input/output devices 1755 (such as one or more displays, speakers, haptic devices, and so on), communication component 1756, and/or other components. The processing unit 1751 may execute instructions stored in the storage media 1753 in order to perform various operations discussed above.

For example, the processing unit 1751 may receive health data from a health sensor 1754 and may store such health data in the storage media 1754. By way of another example, the processing unit 1751 may receive signals from the tightness sensor(s) 1752 and may utilize lookup tables stored in the storage media 1754 to correlate signals to the tightnesses of a band, adjust a measurement obtained from a health sensor, evaluate the signal for changes in the tightness of the band according to operational tolerances of the health sensor that relate to the tightness of the band (which may be stored in the storage media 1754), and so on. The processing unit 1751 may store data regarding such signals, determined tightnesses, history of determined tightnesses, operational tolerances of the health sensor, and so on in the storage media 1754. In examples where the processing unit 1751 determines the tightness of a band, the processing unit 1751 may compare the determined tightness of the band to tightness ranges stored in the storage media 1754 to determine whether or not the determined tightness is within such a range of tightness values. The processing unit 1751 may also provide output (such as a visual output, an audio output, a haptic output, a combination of various outputs, and so on) to a user via the input/output devices 1755 to adjust the band (such as to improve operation of a health sensor).

The wearable electronic device 100 may communicate with one or more other electronic devices, such as the electronic device 1750, via the communication component 1756 over one or more wired and/or wireless communication connections. Similar to the wearable electronic device 100, the electronic device 1750 may include one or more communication components 1757, processing units 1758, storage media 1759, and/or other components. In various examples, the wearable electronic device 100 may transmit data and/or notifications regarding data to the electronic device 1750 via the communication components 1756 and 1757, such as the above discussed health data, signals, output directed to adjust band tightness, determined band tightnesses, history of determined tightnesses, operational tolerances of the health sensor, and so on. The processing unit 1758 may store such data or notifications in the storage media 159.

Alternatively and/or additionally, in some examples, the wearable electronic device 100 and the electronic device 1750 may be configured in a cooperative computing arrangement. As such, the electronic device 1750 may utilize the processing unit 1758 to process the data in one or more of the various ways the processing unit 1751 is described processing such data above. For example, the processing unit 1758 may process received health data to determine health information for a user of the wearable electronic device 100. By way of another example, the storage media 1759 may store one or more lookup tables described above, operational tolerances of the health sensor, and/or other information. As such, the processing unit 1758 may receive signals and utilize the lookup tables to correlate signals to the tightnesses of a band, adjust a measurement obtained from a health sensor, evaluate the signal for changes in the tightness of the band according to operational tolerances of the health sensor that relate to the tightness of the band, and so on. The processing unit 1758 may store the results of such determinations in the storage media 1759, transmit such results to the wearable electronic device 100, and/or perform various other operations As described above and illustrated in the accompanying figures, the present disclosure relates to sensing the tightness of a band attaching a wearable electronic device to a user's body part. A wearable electronic device may include a housing having a processing unit and a health sensor, a band operable to couple the housing to a body part of a user, and a tightness sensor coupled to the band that produces a signal indicative of a tightness of the band on the user's body part. The processing unit may determine a tightness of the band based on the signal and perform various operations based thereon. For example, the processing unit may evaluate the signal for changes in the tightness of the band according to operational tolerances of the health sensor that relate to the tightness of the band. By way of another example, the processing unit may provide output directing the user to adjust the band to improve operation of the health sensor if the tightness of the band is outside a range of tightness values. By way of still another example, the processing unit may monitor changes in tightness of the band and adjust a measurement obtained by the health sensor to account for movement of the body part.

In the present disclosure, the methods disclosed may be implemented as sets of instructions or software readable by a device. Further, it is understood that the specific order or hierarchy of steps in the methods disclosed are examples of sample approaches. In other embodiments, the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may take the form of, but is not limited to, a magnetic storage medium (e.g., floppy diskette, video cassette, and so on); optical storage medium (e.g., CD-ROM); magneto-optical storage medium; read only memory (ROM); random access memory (RAM); erasable programmable memory (e.g., EPROM and EEPROM); flash memory; and so on.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A wearable device, comprising:
   a housing including a processing unit and a health sensor;
   a band operable to couple the housing to a body part of a user; and
   a tightness sensor, coupled to the band and communicably coupled to the processing unit, that produces a signal indicating a tightness of the band;
   wherein the processing unit is configured to:
   determine the tightness of the band using the signal; and if the tightness of the band is outside a range of tightness values, provide output directing the user to adjust the band to improve operation of the health sensor; wherein:

the tightness sensor comprises first and second capacitive plates operable to change proximity with respect to each other in response to a change in the tightness of the band; and the signal indicates a capacitance between the first and second capacitive plates.

2. The wearable device of claim 1, wherein the first and second capacitive plates are operable to change proximity with respect to each other in a direction perpendicular to a lengthwise dimension of the band.

3. The wearable device of claim 1, wherein the first and second capacitive plates are operable to change proximity with respect to each other in a direction along a lengthwise dimension of the band.

4. The wearable device of claim 1, wherein the first capacitive plate is embedded within the band.

5. The wearable device of claim 4, wherein the second capacitive plate is also embedded within the band.

6. A wearable device, comprising:

a housing including a processing unit and a health sensor;

a band operable to couple the housing to a body part of a user; and a tightness sensor, coupled to the band and communicably coupled to the processing unit, that produces a signal indicating a tightness of the band;

wherein the processing unit is configured to:

monitor changes in the tightness of the band using the signal; and adjust a measurement obtained by the health sensor using the changes in the tightness of the band to account for movement of the body part; wherein:

the tightness sensor comprises a series of conductors positioned in the band; and the signal indicates at least one of a resistance or a capacitance between conductors of the series of conductors.

7. The wearable device of claim 6, wherein the signal indicates the resistance between the conductors and the conductors are positioned along a lengthwise dimension of the band.

8. The wearable device of claim 6, wherein the signal indicates the capacitance between the conductors and the conductors are positioned perpendicular to a lengthwise dimension of the band.

9. The wearable device of claim 6, wherein the signal indicates both the resistance and the capacitance between the conductors.

10. The wearable device of claim 6, wherein the series of conductors includes at least three conductors.

11. The wearable device of claim 6, wherein the band surrounds the conductors.

12. The wearable device of claim 6, wherein the band surrounds at least one of the conductors.

13. The wearable device of claim 6, wherein the band separates the series of conductors when the band is unstretched.

14. The wearable device of claim 6, wherein the band separates the series of conductors when the band is stretched.

15. The wearable device of claim 6, wherein the series of conductors comprises:

a first row; and a second row; wherein:

the first row is positioned along a lengthwise dimension of the band above the second row.

16. The wearable device of claim 6, wherein the conductors comprise an isotropically conductive particles.

17. The wearable device of claim 6, wherein the conductors comprise conductive particles.

18. The wearable device of claim 6, wherein the series of conductors comprises:

a first row; and a second row; wherein:

the first row is positioned across from the second row along a widthwise dimension of the band.

19. A wearable device, comprising:

a housing including a processing unit and a health sensor;

a band operable to couple the housing to a body part of a user; and a tightness sensor, coupled to the band and communicably coupled to the processing unit, that produces a signal indicating a tightness of the band; wherein:

the processing unit evaluates the signal for changes in the tightness of the band according to operational tolerances of the health sensor that relate to the tightness of the band;

the tightness sensor comprises a capacitive plate disposed in the band operable to change proximity with respect to the body part of the user in response to a change in the tightness of the band; and the signal indicates a capacitance between the capacitive plate and the body part of the user.

20. The wearable device of claim 19, wherein the band surrounds the capacitive plate.

* * * * *